(12) United States Patent
Weidner-Wells et al.

(10) Patent No.: US 6,579,880 B2
(45) Date of Patent: Jun. 17, 2003

(54) ISOXAZOLES AND OXADIAZOLES AS ANTI-INFLAMMATORY INHIBITORS OF IL-8

(75) Inventors: Michele A. Weidner-Wells, Hillsborough, NJ (US); Todd C. Henninger, Neshanic Station, NJ (US); Dennis J. Hlasta, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/875,840

(22) Filed: Jun. 6, 2001

(65) Prior Publication Data
US 2002/0049213 A1 Apr. 25, 2002

Related U.S. Application Data
(60) Provisional application No. 60/209,744, filed on Jun. 6, 2000.

(51) Int. Cl.$^7$ ............... A61K 31/496; C07D 413/12; C07D 413/14
(52) U.S. Cl. .............. 514/253.1; 514/254.03; 514/254.04; 514/318; 514/326; 514/340; 514/364; 514/378; 544/364; 544/367; 546/194; 546/209; 546/269.4; 546/272.1; 548/131; 548/247; 548/248
(58) Field of Search ............... 544/364, 367; 514/253.1, 254.03, 254.04

(56) References Cited

U.S. PATENT DOCUMENTS

| 5,476,866 A | 12/1995 | Kuo et al. |
| 5,633,272 A | 5/1997 | Talley et al. |
| 5,814,627 A | 9/1998 | Schwab et al. |
| 6,277,872 B1 * | 8/2001 | Brenner et al. ............. 514/364 |

FOREIGN PATENT DOCUMENTS

JP          60054375        3/1985

OTHER PUBLICATIONS

Matsukawa et al. Inflammation Research, 47, Supplement 3, pp. S137–S144 (1998).*
Baggiolini et al.; "Interleukin–8 and Related Chemotactic Cytokines", CHEST Contents, vol. 105, No. 3 (Mar./1994), pp 95S–98S.
Bickel; "The Role of Interleukin–8 in Inflammation and Mechanisms of Regulation", J. Peridontol, vol. 64, No. 5 (May/1993), pp 456–460.
Broaddus et al.; "Neutralization of IL–8 Inhibits Neutrophil Influx in a Rabbit Model of Endotoxin–Induced Pleurisy", Journal of Immunology, 1994, 152, pp 2960–2967.
Coda et al.; "A Simplified Synthesis of Aromatic Hydroximic Acid Chlorides (*)", Gazzetta Chimica Italiana, 114, 1984, pp 131–132.
Horuk; "The interleukin–8 receptor family: from chemokines to malaria", Immunology Today, vol. 15, No. 4 (1994), pp 169–174.

Kemeny et al.; "Role of Interleukin–8 Receptor in Skin", Int. Arch Allergy Immunol. 1994, 104, pp 317–322.
Lemster et al.; "IL–8/IL–8 receptor expression in psoriasis and the response to systemic tacrolimus (FK506) therapy", Clin Exp Immunol 1995, 99, pp 148–154.
Liu et al.; "A Particularly Convenient Preparation of Benzohydroximinoyl Chlorides (Nitrile Oxide Precursors)", Journal of Organic Chemistry, 1980, vol. 45 No. 19, pp 3916–3918.
McGillivray et al., "Chlorinations with t–butyl hypochlorite in the presence of alcohols. Part 1. Preparation of benzohydroximoyl chlorides.", S. Afr. J. Chem. 1986, 39(1), pp 54–56.
Schroder et al.; "The Biology of NAP–1/IL–8, a Neutrophil–Activating Cytokine", In: Granulocyte Responses to Cytokines, Marcel Dekker, NY (1992), pp 387–416.
Strieter et al., "The immunopathology of chemotactic cytokines: The role of interleukin–8 and monocyte chemoattractant protein–1", J. Lab Clin Med 1994, 123, pp 183–197.
Strosberg; "Structure/function relationship of proteins belonging to the family of receptors coupled to GTP–binding proteins", Eur. J. Biochem. 196 (1991), pp 1–10.
Wu et al.; "G Protein–Coupled Signal Transduction Pathways for Interleukin–8", Science, vol. 261, 1993, pp 101–103.
Zwahlen et al.; "In Vitro and in Vivo Activity and Pathophysiology of Human Interleukin–8 and Related Peptides", Int. Rev. of Experimental Pathology, vol. 34B (1993), pp 27–42.

* cited by examiner

*Primary Examiner*—Emily Bernhardt

(57) ABSTRACT

The invention relates to isoxazole and oxadiazole compounds of Formulae I and II,

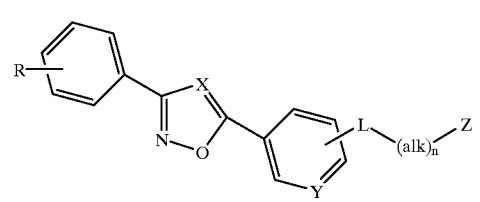

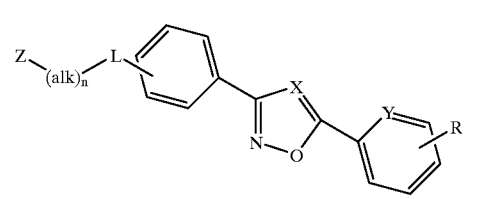

pharmaceutical compositions containing the compounds, and methods for their production and use. These compounds are effective in inhibiting the action of IL-8 and are thus useful as anti-inflammatory agents for a variety of diseases.

15 Claims, No Drawings

ISOXAZOLES AND OXADIAZOLES AS ANTI-INFLAMMATORY INHIBITORS OF IL-8

CROSS REFERENCE TO RELATED APPLICATION

The present application claims the benefit of provisional application Ser. No. 60/209,744 filed Jun. 6, 2000, the contents of which are hereby incorporated by reference into the present application.

FIELD OF THE INVENTION

The present invention relates to isoxazole and oxadiazole compounds having anti-inflammatory activity, pharmaceutical compositions that contain the compounds, and methods for their production and use.

BACKGROUND OF THE INVENTION

Interleukin-8 (IL-8) is a chemotactic cytokine whose primary role seems to be to chemoattract and activate polymorphonuclear leukocytes (PMN; neutrophil). Inhibition of the actions of IL-8 on the neutrophil is expected to inhibit their recruitment to sites of inflammation, their activation, and thus inhibit the release of neutrophil products such as lysosomal enzymes (elastase, myeloperoxidase, cathepsins, etc.) which are responsible for much of the tissue damage associated with inflammation.

IL-8 is a member of the C-X-C family of chemokines which includes platelet factor 4 (PF4), neutrophil activating peptide-2 (NAP-2), melanoma growth stimulatory activity (MGSA) chemokines, interferon-γ induced peptide (IP-10), and the like (reviewed in Kemeny et al., *Skin. Int. Arch. Allergy Immunol.* 104:317–22, 1994; Schroder, J. & E. Christophers, "The Biology of NAP-1/IL-8, a Neutrophil-Activating Cytokine," In: *Granulocyte Responses to Cytokines*, Marcel Dekker, N.Y., pp. 387–416, 1992.; Bickel, M., *J. Periodontal.* 64:456–460, 1993.; Baggiolini et al., *Chest* 105(Suppl. 3):955–85, 1994). IL-8 is produced primarily by monocytes and macrophages, but is also produced by a variety of other cell types including synovial cells and keratinocytes (Schroder, J. & E. Christophers, supra; Kemeny et al., supra). Its production can be triggered by inflammatory stimuli such as IL-1, TNFα, LPS, and IL-4, (Streiter et al., *J. Lab. Clin. Med.* 123:183–97, 1994; Zwahlen et. al., *Int. Rev. Exp. Pathol.* 348, 27–42, 1993). IL-8 is a potent chemotactic agent for neutrophils, and can stimulate neutrophil degranulation and induce basophil histamine release (reviewed in Kemeny et al., supra). Neutrophils are prime players in the inflammatory response and responsible for extensive tissue damage due to the release of lysosomal enzymes. High levels of IL-8 have been detected in lavage fluids of cystic fibrosis patients, sites of atherosclerosis and ischemic reperfusion injury, in the synovial fluid and cells from rheumatoid arthritis patients and also in psoriatic plaques (Streiter et al., supra; reviewed in Kemeny et al., supra; Lemster et al., *Clin. Exp. Immunol.* 99:148–154, 1995). If IL-8 activity can be inhibited by preventing its binding to cell surface receptors, neutrophils can be prevented from accumulating at the site of inflammation.

Specificity of IL-8 activation occurs through specific cell surface receptors (Horuk, R. The Interleukin-8 receptor Family: From Chemokines to Malaria. *Immunology Today*, 1994; Strosberg, A. D., *Eur. J. Biochem.* 196:1–10, 1991). IL-8 receptors have 7 transmembrane domains, are members of the rhodopsin family of receptors, and are linked to G-proteins for signal transduction (Baggiolini et al., supra; Wu et al., *Science* 261:101–3, 1993). Knockout mouse studies of the IL-8 receptor have shown a lack of neutrophil migration in vivo in response to an inflammatory signal, demonstrating the importance of this cytokine in inflammation (Moore, M., The Role of the Murine IL-8 Receptor and its Ligand in Chemotaxis and Inflammation, *IRA Meeting*, January 1995). Neutralizing antibody studies have also shown a decrease in neutrophil migration by inhibiting IL-8 binding to the neutrophil receptor (Broaddus et al., *J. Immunol.* 152:2960–7, 1994). Clinical indications for the use of an IL-8 receptor antagonist include: adult respiratory distress syndrome (ARDS), rheumatoid arthritis (RA), myocardial perfusion injury, ulcerative colitis, psoriasis, chronic obstructive lung disease (COPD), cystic fibrosis (CF), and some cancers which have been shown to involve high levels of IL-8 production.

Isoxazoles have been reported to be useful as antagonists of the platelet glycoprotein IIb/IIIa fibrinogen receptor complex or the vitronectin receptor for the inhibition of platelet aggregation, as thrombolytics, and/or for the treatment of thromboembolic disorders. 4,5-Dihydronaphth[1,2-c] isoxazole derivatives are reported to be useful as serotonin 5-HT$_3$ antagonists useful for the treatment of anxiety, psychiatric disorders, nausea, vomiting and drug dependency. Isoxazole derivatives are also reported to be useful as herbicides.

JP 60054375 (Chisso Corp., Japan, 1985) discloses, among other compounds, isoxazoles of the formula

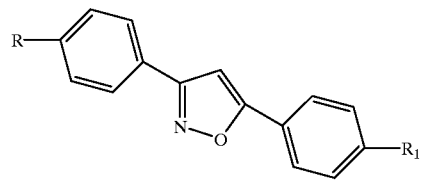

wherein substituents are as described in the reference, which are stated to be "useful as liq. crystal components."

U.S. Pat. No. 5,476,866 to Kuo et al. discloses isoxazoles of the formula

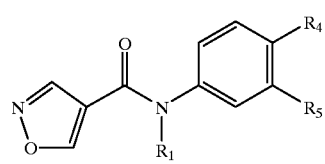

wherein substituents are as described in the reference, which are stated to have "anti-proliferative, anti-inflammatory and anti-tumor activity."

U.S. Pat. No. 5,633,272 to Talley et al. discloses substituted isoxazolyl compounds of the formula

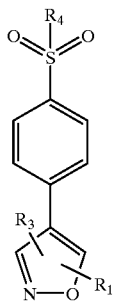

wherein substituents are as described in the reference, which are stated to be useful "in treating inflammation and inflammation-related disorders."

U.S. Pat. No. 5,814,627 to Schwab et al. discloses 3,5-disubstituted and 3,4,5-trisubstituted 2-isoxazolines and isoxazoles of the formula

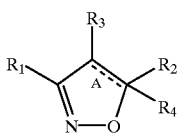

wherein substituents are as described in the reference, which are stated to be "suitable for preparing medicaments for the therapy of inflammations, asthma, rheumatoid diseases and auto-immune diseases."

SUMMARY OF THE INVENTION

The invention provides a compound of Formula I or II,

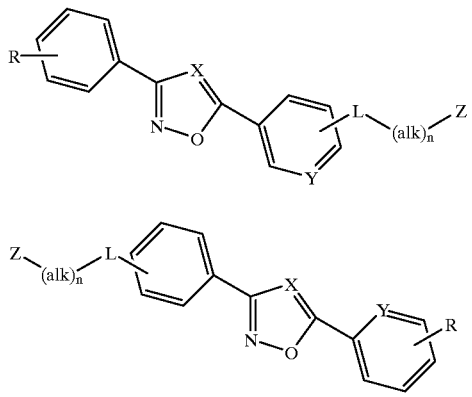

wherein
R is one or two independent members selected from hydrogen, halogen, $C_{1-6}$ alkyl, $C_{1-6}$alkoxy, alkoxycarbonyl, aryl, aryloxy, hydroxy, nitro, sulfonylamino, trifluoromethyl, cyano, methylenedioxy, and ethylenedioxy;

X is nitrogen or $CR_1$ wherein $R_1$ is selected from hydrogen, alkyl, aryl, halogen, $CH_2OH$, carbomethoxy, and carboethoxy;

Y is CR or nitrogen;

L is selected from oxygen, sulfur, —N($R_2$)—, —C(O)N$R_2$—, —$R_2$NC(O)—, —C(O)O—, and —OC(O)—, wherein $R_2$ is hydrogen or $C_{1-6}$alkyl; and Z is $NR_3R_4$ or saturated heterocyclyl having one or two nitrogen as heteroatom, wherein $R_3$ and $R_4$ are independently selected from hydrogen, $C_{1-6}$alkyl, and phenyl and the heterocyclyl group may be substituted with one or more independent substituents selected from halogen, oxo, OH, alkyl, amino and alkoxy;

Alk is a branched or unbranched alkyl group;

n is an integer from 0–6 representing the number of carbons in the alkylene group, with the proviso that when L is oxygen, sulfur, or nitrogen, n is an integer from 2–6;

or an optical isomer, enantiomer, diastereomer, racemate or racemic mixture thereof, or a pharmaceutically acceptable salt thereof.

Compounds of the above formulae are useful as anti-inflammatory agents for the treatment of adult respiratory distress syndrome (ARDS), rheumatoid arthritis (RA), myocardial perfusion injury, ulcerative colitis, psoriasis, chronic obstructive lung disease (COPD), cystic fibrosis (CF), and cancers in a subject such as human and animal.

The present invention is also directed to a method of treating a subject having a condition caused by or contributed to by action of IL-8, which comprises administering to said subject a therapeutically effective amount of a compound of Formula I or II.

The present invention is further directed to a method of preventing a subject from suffering from a condition caused by or contributed to by action of IL-8, which comprises administering to the subject a prophylactically effective amount of a compound of Formula I or II.

Other objects and advantages will become apparent to those skilled in the art from a review of the ensuing specification.

DETAILED DESCRIPTION

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. For example, alkyl radicals include methyl, ethyl, n-propyl, isopropyl, n-butyl, isobutyl, sec-butyl, t-butyl, n-pentyl, 3-(2-methyl) butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. The alkyl group and alkoxy group may be independently substituted with one or more members of the group including, but not limited to, (mono-, di-, tri-, or per-halogen, alkyl, alkoxy, aryl, amino, OH, CN, mercapto, nitro, and $C_{1-8}$acyloxy.

The term "halo" or "halogen" means fluoro, chloro, bromo and iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, $C_1$–$C_8$-alkyl, $C_1$–$C_8$-alkoxyl, thio-$C_1$–$C_8$-alkyl, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Unless specified otherwise, "heterocyclyl" or "heterocycle" is a 3- to 8-member saturated, partially saturated, or unsaturated single or fused ring system which consists of carbon atoms and from one to three heteroatoms selected from N, O and S. The heterocyclyl group may be attached at any heteroatom or carbon atom which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, $C_1$–$C_{10}$ alkyl, amino, and alkoxy.

Whenever the term "alkyl", "acyl", or "aryl" or either of their prefix roots appear in a name of a substituent (e.g., aralkyl, dialkylamino) it shall be interpreted as including those limitations given above for "alkyl", "acyl", and "aryl." Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Whether used alone or as part of a substituent group, "heteroaryl" refers to a cyclic aromatic radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms, for example, pyridinyl, pyrazinyl, pyrimidinyl, pyrrolyl, pyrazolyl, imidazolyl, thiazolyl, oxazolyl, isoxazolyl, thiadiazolyl, triazolyl, oxadiazolyl, thienyl, furanyl, quinolinyl, isoquinolinyl, and the like. The heteroaryl group may be substituted by independent replacement of 1 to 3 of the hydrogen atoms thereon with halogen, OH, CN, mercapto, nitro, amino, $C_1$–$C_8$-alkyl, $C_1$–$C_8$-alkoxyl, thio-$C_1$–$C_8$-alkyl, $C_1$–$C_8$-alkyl-amino, di($C_1$–$C_8$-alkyl)amino, (mono-, di-, tri-, and per-) halo-alkyl, formyl, carboxy, alkoxycarbonyl, $C_1$–$C_8$-alkyl-CO—O—, $C_1$–$C_8$-alkyl-CO—NH—, or carboxamide. Heteroaryl may be substituted with a mono-oxo to give for example a 4-oxo-1H-quinoline.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

From Formulae I and II, it is evident that some compounds of the present invention may have at least one stereogenic center, they may accordingly exist as enantiomers. Where the compounds possess two or more stereogenic centers, they may additionally exist as diastereomers. It is intended that the present invention include within its scope the stereochemically pure isomeric forms of the compounds as well as their racemates. Furthermore, some of the crystalline forms for the compounds may exist as polymorphs and as such are intended to be included in the present invention. In addition, some of the compounds may form solvates with water (i.e., hydrate, hemihydrate and sesquihydrate forms) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base which possess the desired pharmacological activity of the free base and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

The term "subject" includes, without limitation, any animal or artificially modified animal. As a particular embodiment, the subject is a human.

The compounds described in the present invention possess anti-inflammatory activity as IL-8 antagonists, thus inhibiting neutrophil accumulation at the site of inflammation and ultimately, inhibiting the release of neutrophil products responsible for much of the tissue damage associated with inflammation in humans and animals.

In particular, compounds of Formula I or II wherein Z is a saturated heterocyclyl having only one or two nitrogen as heteroatom are particular embodiments of the present invention for such purposes.

Compounds of Formula I or II wherein Z is NR$_3$R$_4$ and R$_3$, R$_4$ are as described above are also particular embodiments of this invention. More particularly, R$_3$ and R$_4$ are alkyl or substituted alkyl.

Compounds of Formula I or II wherein R is one or two independent members selected from hydrogen, halogen, $C_{1-6}$alkyl, $C_{1-6}$alkoxy, alkoxycarbonyl, phenyl, phenyloxy, hydroxy, nitro, sulfonylamino, trifluoromethyl, cyano, methylenedioxy, and ethylenedioxy are also particular embodiments of this invention.

Compounds of Formula I or II wherein X is CH are further particular embodiments of this invention. More particularly, Z is

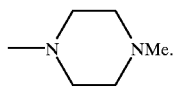

Still more particularly, compounds of Formula II

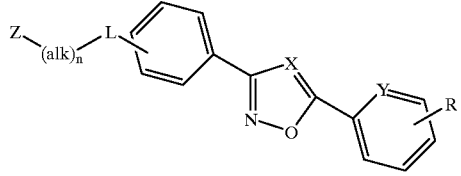

wherein Z, L, X, Y, R and n are as described above are embodiments of this invention. More particularly, X is CH; Z is

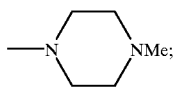

R is halogen. More particularly, R is 4-Cl.

The following are preferred embodiments of the present invention for such purposes:

- piperazine, 1-[3-[4-[5-(4-chlorophenyl)-3-isoxazolyl] phenoxy]propyl]-4-methyl-;
- piperazine, 1-[3-[4-[3-(4-chlorophenyl)-5-isoxazolyl] phenoxy]propyl]-4-methyl-;
- piperazine, 1-[3-[4-[3-[4-(1,1-dimethylethyl)phenyl]-5-isoxazolyl]phenoxy]propyl]-4-methyl-;
- piperazine, 1-[3-[4-[3-[4-chloro-3-(trifluoromethyl) phenyl]-5-isoxazolyl]phenoxy]propyl]-4-methyl-;
- piperazine, 1-[3-[4-[3-(4-fluorophenyl)-5-isoxazolyl] phenoxy]propyl]
- piperazine, 1-[3-[4-[3-(4-chlorophenyl)-1,2,4-oxadiazol-5-yl]phenoxy]propyl]-4-methyl-;
- piperazine, 1-[3-[4-[3-(4-chlorophenyl)-1,2,4-oxadiazol-5-yl]phenoxy]propyl]-;
- 1-propanamine, 3-[4-[5-(4-chlorophenyl)-3-isoxazolyl] phenoxy]-N, N-dimethyl-; and
- 1,3-propanediamine, $N^1$-[5-[3-(4-chlorophenyl)-1,2,4-oxadiazol-5-yl]-2-pyridinyl]-$N^3$, $N^3$-dimethyl-.

This invention also provides processes for preparing the instant compounds. The compounds of Formulae I and II may be prepared from starting materials such as substituted benzaldehydes, arylacetylenes, heteroarylacetylenes, 4-iodophenoxyacetate, trimethylsilylacetylene (TMS-CCH), substituted nitrile, and chloro oxime, which are either readily available or may be easily prepared by methods well known in the art. Outlined in the following schemes are representative procedures to prepare the compounds of the instant invention.

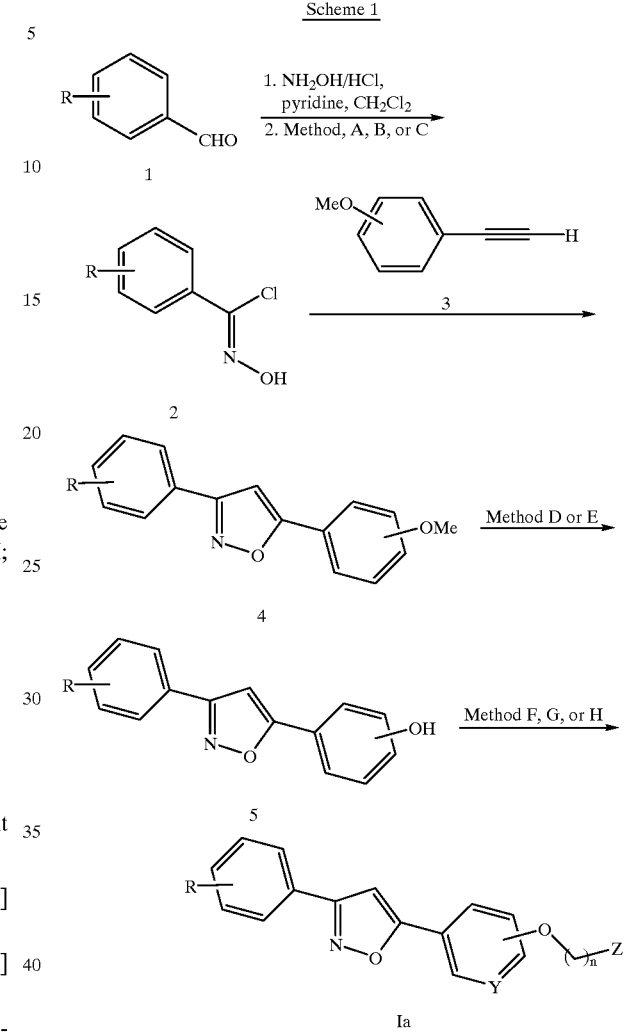

In accordance with Scheme 1, wherein Z, Y, and R are as described above, the appropriately substituted benzaldehyde 1 is converted into the oxime utilizing standard techniques known in the art (such as in the presence of $NH_2OH/HCl$ and pyridine in a suitable solvent such as $CH_2Cl_2$). The oxime is then transformed into the chloro oxime 2 by reaction with N-chlorosuccinimide (Method A) according to the procedure of Liu, Howe and Shelton (K. Liu; B. Shelton; R. K. Howe *J. Org. Chem.*, 1980, 45, 3916). The oxime may be chlorinated with concentrated hydrochloric acid and bleach in dioxane (Method B) according to the conditions of Coda and Tacconi (A. Coda and G. Tacconi Gazz. *Chim. Ital.*, 1984, 114, 131). In addition, the chloro oxime may be generated by the reaction of the oxime with t-butylhypochlorite in 2-propanol and 1,2-dichloroethane (Method C) according to the procedure of McGillivray and ten Krooden (S. Afr. J. Chem., 1986, 39, 54). In situ dehydrohalogenation of the chloro oxime 2 with a tertiary amine base such as triethylamine (TEA) generates the nitrile oxide, which undergoes a [3+2] cycloaddition reaction with methoxyphenyl acetylene 3 to afford the isoxazole nucleus 4. The methyl ether 4 is deprotected to yield phenol 5 with either a suitable reagent such as boron tribromide in an appropriate solvent such as methylene chloride at a temperature preferably from 0° C. to ambient temperature (Method D) or pyridine hydrochloride at a temperature preferably from 180 to 220° C. (Method E). The phenol 5 may be converted into the desired amines Ia by one of several methods. Method F consists of direct alkylation of the phenol 5 with an appropriate amino halide or hydrochloride salt of the amino halide such as Cl—(CH$_2$)$_n$—NR$_3$R$_4$. HCl utilizing an appropriate base such as potassium carbonate in a suitable solvent, such as dimethylformamide (DMF), at a temperature preferably from 80 to 100° C. Method G consists of formation of the alkoxide with an appropriate base such as sodium hydride and alkylation with an appropriate amino halide such as Cl—(CH$_2$)$_n$—NR$_3$R$_4$ in a suitable solvent such as DMF at a temperature preferably from 80–100° C. Method H consists of alkylation of the phenol 5 with the appropriate length dihalide in a suitable solvent such as DMF at a temperature preferably from 80 to 100° C. The resulting halide may be then reacted with the necessary amine in a suitable solvent such as DMF at elevated temperatures.

Scheme 2

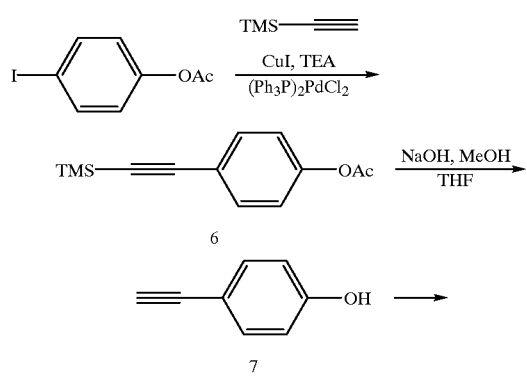

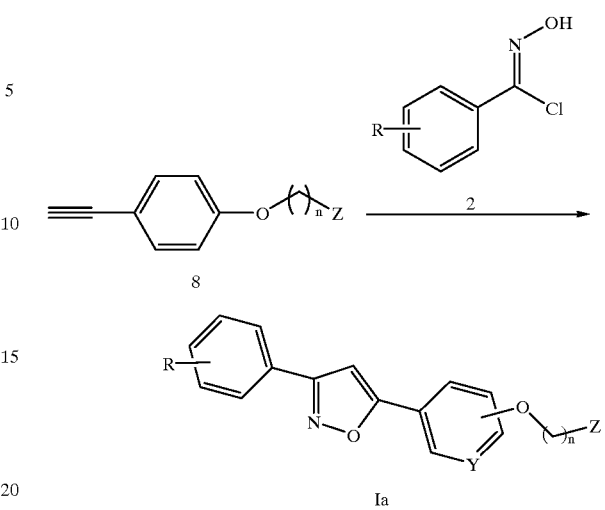

Alternatively, amines Ia can be prepared in accordance with Scheme 2 wherein Z, Y, and R are as described above. 4-Iodophenoxyacetate is converted by standard methods (as shown in the scheme) to the acetylene derivative 6, which is deprotected to afford 4-hydroxyphenylacetylene 7. Alkylation with an appropriate chloroamine in a suitable solvent such as DMF at a temperature preferably from 80 to 120° C. in the presence of a suitable base, such as K$_2$CO$_3$, yields the desired substituted phenoxy derivative 8. This then undergoes a [3+2] cycloaddition reaction with the appropriate chloro oxime 2 preferably in the presence of 4A molecular sieves to produce amines Ia.

Scheme 3

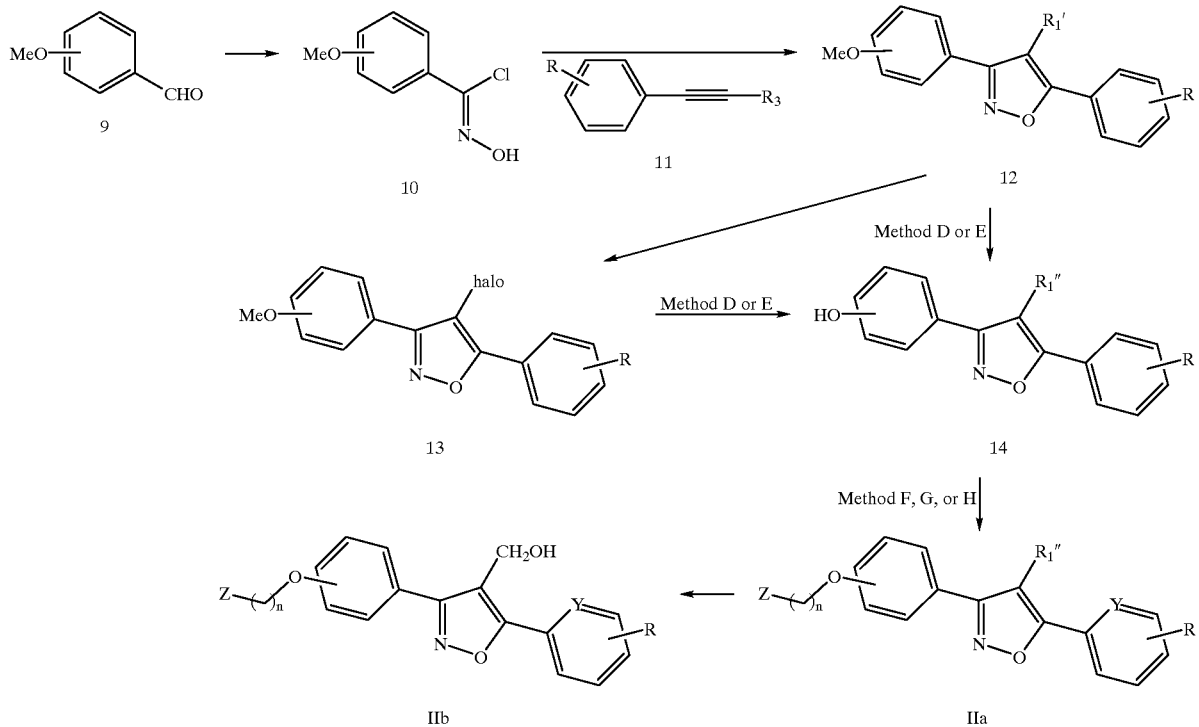

In accordance with Scheme 3, wherein R$_1$' is selected from hydrogen, carbomethoxy, and carboethoxy, R$_1$" is selected from hydrogen, halogen, carbomethoxy, and carboethoxy, Z is NR$_3$R$_4$ and Y, R, R$_1$, R$_3$, and R$_4$ are as described above, methoxybenzaldehyde 9 is converted into the chloro oxime 10 (Scheme 3), which may be reacted with the appropriately substituted phenyl acetylene 11 (or heteroaryl acetylene, such as 2-pyridylacetylene) to give isoxazole 12. At this point, modification of the C-4 position of the isoxazole 12 may be achieved. For instance, a bromine or chlorine atom can be introduced at the C-4 position by bromination or chlorination of the C-4 unsubstituted isoxazole 12 (R$_1$'=H) with N-bromosuccinimide (NBS) or N-chlorosuccinimide (NCS) in a suitable solvent such as DMF to yield 13. Either isoxazole 12 or 13 can then be transformed, in several steps, to the target amines IIa in a sequence analogous to Methods D through H described previously. In addition, reduction of an ester functionality at C-4 (i.e., R$_1$'=CO$_2$Et) with an appropriate reducing agent such as lithium aluminum hydride (LAH) in a suitable solvent such as tetrahydrofuran (THF) affords the alcohol derivative IIb.

Alternatively, where the L—(CH)$_2$—Z moiety is an alkoxy functionality wherein Z is a saturated heterocyclyl having only one or two nitrogen as heteroatom, it can be introduced via a nucleophilic aromatic substitution reaction in accordance with Scheme 4,. Chloro oxime 15, converted from 4-fluorobenzaldehyde as discussed previously, undergoes a [3+2] cycloaddition reaction with the appropriately substituted arylacetylene 11 in the presence of a suitable base such as TEA in an appropriate solvent such as EtOAc to afford isoxazole 16. Displacement of the fluorine occurs readily in the presence of a suitable base such as NaH in an appropriate solvent such as DMF with appropriate amino alcohol at a temperature preferably from 100–110° C. to yield target amines IIc.

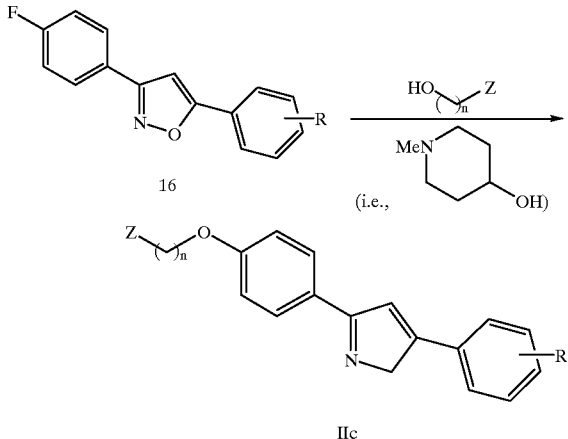

Scheme 4

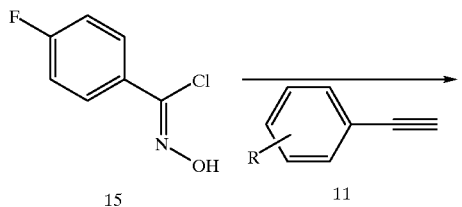

Scheme 5

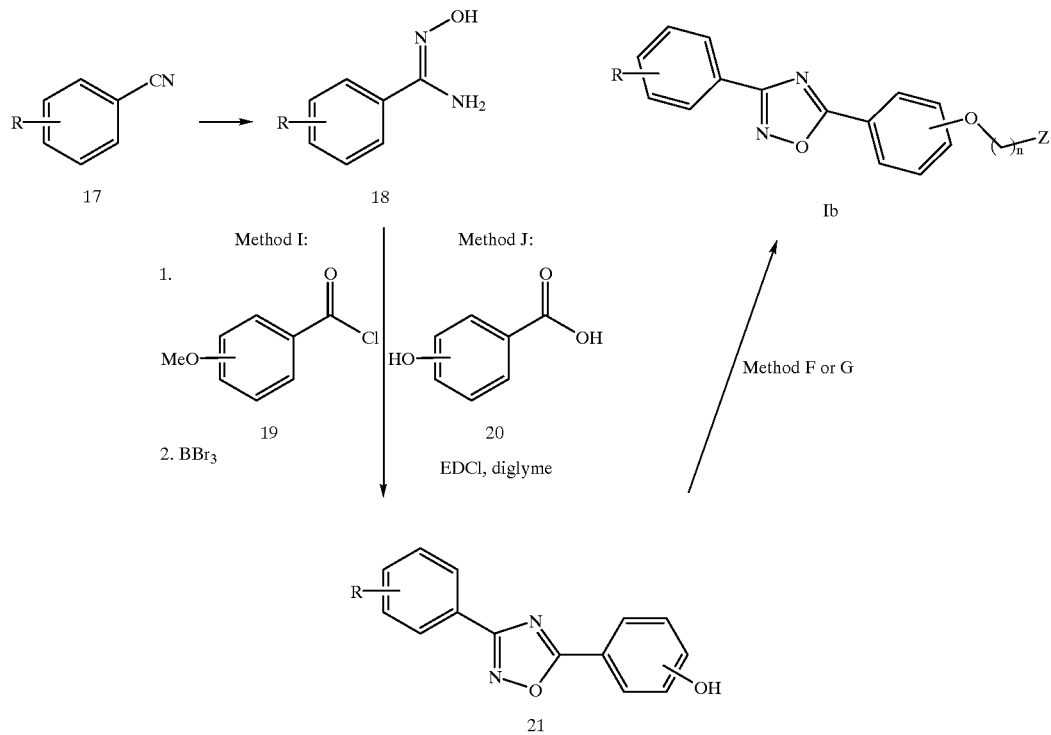

In accordance with Scheme 5, oxadiazole compounds can be prepared by reacting the appropriately substituted nitrile 17 with hydroxylamine at elevated temperatures in an appropriate solvent such as EtOH and H₂O to afford the amide oxime 18, which is then converted into oxadiazole 21 by a two-step process consisting of reacting 18 with acid chloride 19 in the presence of a suitable base such as pyridine at an elevated temperature followed by demethylation of the phenol with a suitable reagent such as boron tribromide in methylene chloride at a temperature preferably from 0° C. to ambient temperature (Method I). Alternatively, amide oxime 18 may be directly converted into oxadiazole 21 by reaction with acid 20 in the presence of a suitable condensing agent such as EDCl at elevated temperature (Method J). Phenol 21 may be alkylated either by Method F or Method G (as discussed previously) to yield target amines Ib.

methyl ester 22 by standard methodology. However, other suitable protecting groups for a carboxylic acid may be utilized. The carbomethoxy benzaldehyde 22 is converted to the chloro oxime 23 as described in Scheme 1. The chloro oxime 23 undergoes a cycloaddition reaction with the appropriate phenyl acetylene derivative 11 to afford isoxazole 24 as described in Scheme 3. The ester 24 is saponified to the corresponding acid 25 with a suitable base such as sodium hydroxide in an appropriate solvent such as MeOH, followed by treatment of an inorganic acid such as HCl. Alternatively, the ester can be converted into the acid by other reagents and conditions which are apparent to those skilled in the art of organic synthesis. The acid 25 may be converted to the corresponding acid chloride with an activating agent such as oxalyl chloride and a catalytic amount of DMF in a suitable solvent such as CH₂Cl₂. The acid chloride is then coupled with the appropriate diamine to yield IId. In some cases, the terminal amine may have to be protected prior to the amide bond formation and then deprotected after the amide bond formation. Once again the amide bond formation can be achieved with other reagents/conditions, such as carbonyl diimidazole, and other peptide coupling reagents, and this is readily apparent to one skilled in the art of organic synthesis.

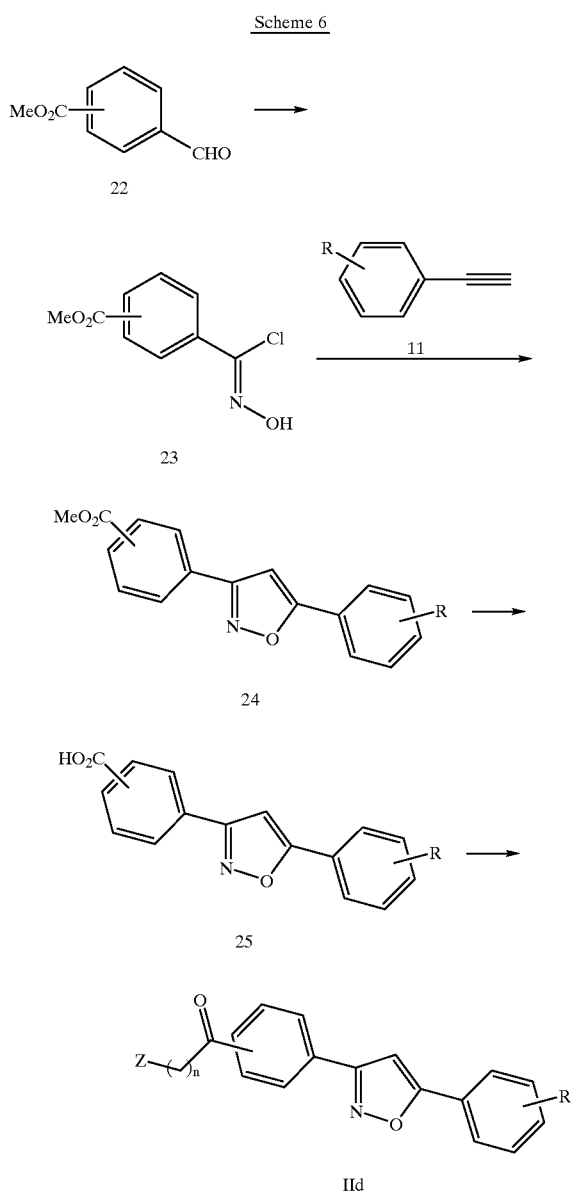

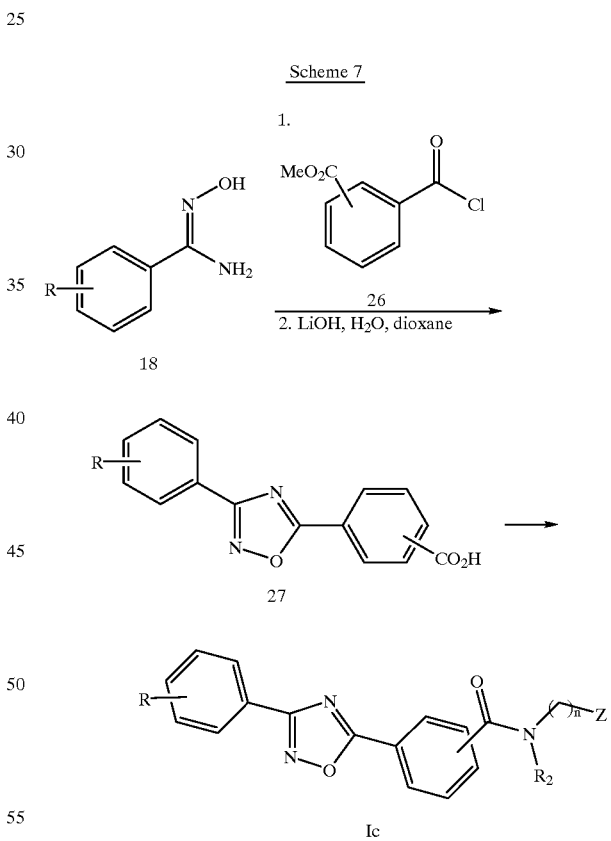

Compounds where L is a carbonyl moiety can be prepared in accordance with Scheme 6, wherein Z and R are as described above. The carboxylic acid is protected as a In accordance with Scheme 7, wherein Z, R, and R₂ are as described above, the amide oxime 18 is converted to the oxadiazole nucleus by reaction with acid chloride 26 in the presence of a suitable base/solvent such as pyridine. The ester is deprotected to afford acid 27 in the presence of a suitable base such as LiOH in a suitable solvent and/or co-solvent such as H₂O and dioxane. This is activated with a suitable activating agent such as oxalyl chloride and then reacted with the appropriate amine in a suitable solvent such as CH₂Cl₂ to give amide Ic.

Scheme 8

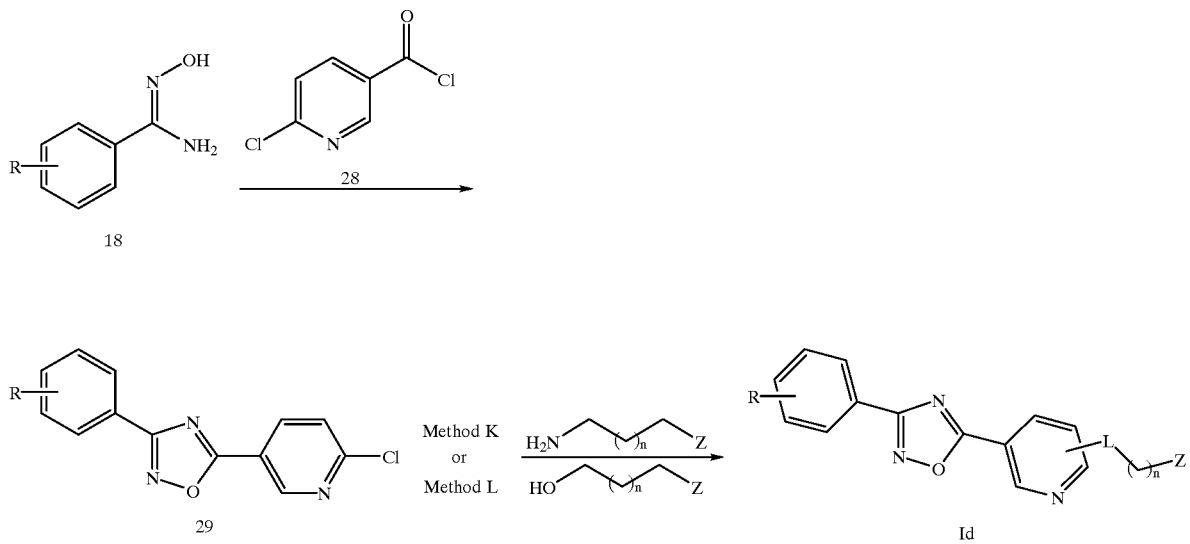

In accordance with Scheme 8, wherein L is oxygen, sulfur, or nitrogen, and R and Z are as described above, the appropriately substituted amide oxime 18 may be condensed with acid chloride 28 in the presence of a suitable base/solvent such as pyridine to afford oxadiazole nucleus 29. The chloride is then displaced with the appropriate amine (Method K) or the amino alcohol in the presence of a suitable base such as NaH in a suitable solvent such as DMF (Method L) to afford targets Id.

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substitutents employed will be apparent to one skilled in the art, as will be the selection of protecting groups where needed.

IL-8 is a C-x-C chemokine which is chemotactic for neutrophils, causing them to attach to the vascular endothelium and then migrate to sites of inflammation. Blockade of ligand binding to the receptor (a G-protein coupled receptor) by a test compound will likely result in a reduction in the number of neutrophils which migrate to the site of inflammation, and subsequently reducing the amount of tissue destructive pro-inflammatory enzymes and inflammatory mediators released by neutrophils. This would result in an anti-inflammatory action.

A radio labeled receptor binding assay may be conducted in purified human neutrophils using $I^{125}$IL-8 as ligand (prepared by dissolving 100 $\mu$Ci in 40 ml binding buffer) (RPMI plus 20% HEPES and 10 mg/ml BSA) and counting the activity in Flashplates (NEN). Neutrophils are purified from fresh human blood by dextran sedimentation in an equal volume of 3% dextran in saline for 30 minutes. After sedimentation, the blood is centrifuged for 10 minutes at 1000 rpm at 4° C. and the supernate is aspirated and discarded. The cells are resuspended in 0.2% saline for 30 seconds to lyse the red blood cells remaining, and isotonicity is re-established by the addition of 1.6% saline in an equal volume. Ten mls ficoll is underlaid of the blood and the sample is centrifuged for 40 minutes at 1400 rpm at 25° C. After centrifugation, the supernate is removed and the cells re-suspended for cell counting. Cell volume is adjusted to $8 \times 10^5$ cells/ml in binding buffer without BSA.

The experiment is conducted by adding 50 $\mu$L binding buffer to each well of the flashplate, followed by 5 $\mu$L of the test drug sample (in 26% DMSO/HEPES buffer), 20 $\mu$L of the $I^{125}$-IL-8 ligand (final concentration =0.125 nM), and 125 $\mu$L of the cell suspension. The plates are then incubated at 37° C. for 60 minutes and the supernate is aspirated to within 2 mm of the bottom of the well. The plates are then sealed and counted for 1 minute in a Packard TopCount.

Drug treated wells are compared to vehicle treated wells for inhibition of binding as determined by a decrease in dpm as compared to the vehicle wells. Unlabelled IL-8 serves as the standard antagonist and has an $IC_{50}$ of approximately 1 nM.

% Inhibition is calculated as follows:

$$\% \text{ Inhibition} = 1 - \frac{DPM \text{ test compound}}{DPM \text{ vehicle control}} \times 100$$

$IC_{50}$ is calculated using K-Graph.

As set forth in the following tables, some compounds of the present invention were tested in the above binding assay, and their biological activity ($IC_{50}$, $\mu$M), mass spectra data, and methods of preparation are reported.

TABLE 1

Biological activity and mass spectra data of compound No. 1–18

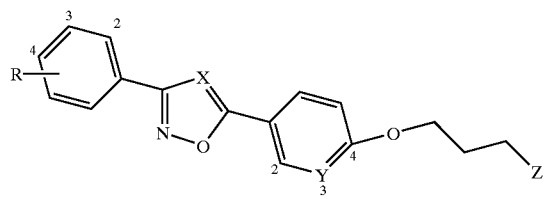

| No. | R | X | Y | Z | IC$_{50}$ | MS | Methods |
|---|---|---|---|---|---|---|---|
| 1 | H | CH | CH | NMe$_2$ | 6.7 | 323 (M + 1) | A, D, F |
| 2 | 4-Cl | CH | CH | NMe$_2$ | 3.9 | 357 (M + 1), 359 | A, D, F |
| 3 | 4-OMe | CH | CH | –N(piperazine)NMe | 6.9 | 408 (M + 1) | Scheme 2 |
| 4 | 4-tBu | CH | CH | –N(piperazine)NMe | 2.7 | 434 (M + 1) | Scheme 2 |
| 5 | 4-CF$_3$ | CH | CH | –N(piperazine)NMe | 6.0 | 446 (M + 1) | Scheme 2 |
| 6 | 3,4-OCH$_2$O | CH | CH | –N(piperazine)NMe | 4.7 | 422 (M + 1) | Scheme 2 |
| 7 | 4-Cl | CH | CH | –N(piperazine)NMe | 2.1 | 412 (M + 1), 414 | Scheme 2 |
| 8 | 3-CF$_3$, 4-Cl | CH | CH | –N(piperazine)NMe | 2.7 | 480 (M + 1), 482 | Scheme 2 |
| 9 | 4-F | CH | CH | –N(piperazine)NMe | 2.0 | 396 (M + 1) | Scheme 2 |
| 10 | H | CH | CH | –N(piperazine)NMe | 3.0 | 378 (M + 1) | Scheme 2 |
| 11 | 3-Cl | CH | CH | –N(piperazine)NMe | 9.6 | 412 (M + 1), 414 | Scheme 2 |
| 12 | 4-PhO | CH | CH | –N(piperazine)NMe | 22.7 | 470 (M + 1) | Scheme 2 |
| 13 | 4-CO$_2$Me | CH | CH | –N(piperazine)NMe | 21% @ 25 μM | 436 (M + 1) | B, D, G |

TABLE 1-continued
Biological activity and mass spectra data of compound No. 1–18
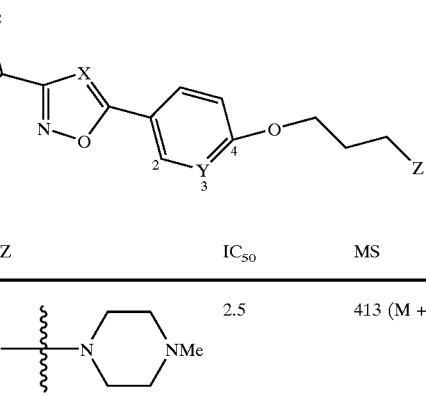
| No. | R | X | Y | Z | IC$_{50}$ | MS | Methods |
|---|---|---|---|---|---|---|---|
| 14 | 4-Cl | N | CH | 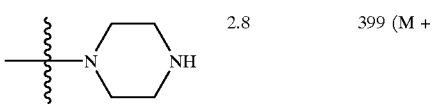 | 2.5 | 413 (M + 1), 415 | I, F |
| 15 | 4-Cl | N | CH | 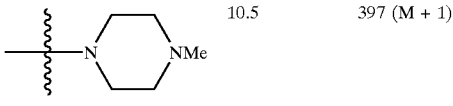 | 2.8 | 399 (M + 1), 401 | I, H |
| 16 | 4-F | N | CH | 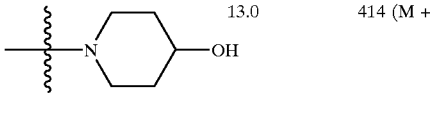 | 10.5 | 397 (M + 1) | I, H |
| 17 | 4-Cl | N | CH | 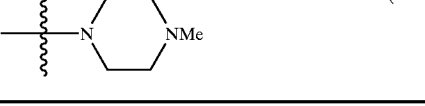 | 13.0 | 414 (M + 1), 416 | I, H |
| 18 | 4-Cl | N | COMe | | 7.53 | 443 (M + 1), 445 | J, F |
TABLE 2
Biological activity and mass spectra data of compound No. 19–42
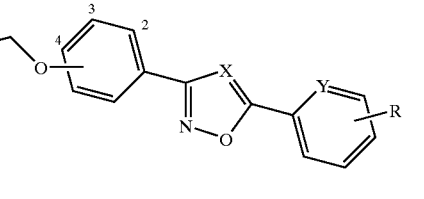
| No. | Pos | m | X | Z | R | Y | IC$_{50}$ | MS | Methods |
|---|---|---|---|---|---|---|---|---|---|
| 19 | 4 | 1 | CH | NMe$_2$ | 4-Me | CH | 5.1 | 337 (M + 1) | A, D, F |
| 20 | 4 | 1 | CH | NMe$_2$ | H | CH | 10.6 | 323 (M + 1) | A, D, F |
| 21 | 4 | 1 | CH | NMe$_2$ | 4-Cl | CH | 2.7 | 357 (M + 1), 359 | A, D, F |
| 22 | 4 | 1 | CH | NMe$_2$ | 4-F | CH | 3.1 | 341 (M + 1) | A, D, G |
| 23 | 4 | 1 | CH |  | H | CH | 5.4 | 363 (M + 1) | A, D, F |

TABLE 2-continued

Biological activity and mass spectra data of compound No. 19–42

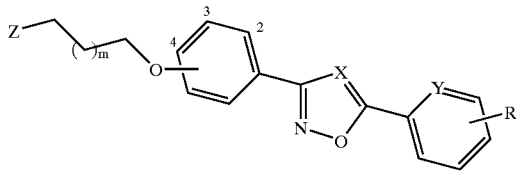

| No. | Pos | m | X | Z | R | Y | IC$_{50}$ | MS | Methods |
|---|---|---|---|---|---|---|---|---|---|
| 24 | 4 | 0 | CH | NMe$_2$ | H | CH | 18.8 | 309 (M + 1) | A, D, F |
| 25 | 4 | 1 | CH | —N(piperazine)NMe | H | CH | 6.2 | 378 (M + 1) | A, D, F |
| 26 | 4 | 1 | CH | NMe$_2$ | 4-NO$_2$ | CH | 12.1 | 368 (M + 1) | A, D, F |
| 27 | 4 | 1 | CH | —N(piperazine)NMe | 4-Cl | CH | 1.6 | 412 (M + 1), 414 | A, D, F |
| 28 | 4 | 1 | CBr | NMe$_2$ | H | CH | 10.9 | 401 (M + 1), 403 | A, D, F, J |
| 29 | 4 | 1 | CCl | NMe$_2$ | H | CH | 6.0 | 357 (M + 1), 359 | A, D, F, J |
| 30 | 4 | 1 | CCH$_2$OH | NMe$_2$ | H | CH | 25 | 353 (M + 1) | A, D, F |
| 31 | 4 | 1 | CCO$_2$Et | NMe$_2$ | H | CH | 25 | 395 (M + 1) | A, D, F |
| 32 | 3 | 1 | CH | NMe$_2$ | 4-Cl | CH | 8.1 | 357 (M + 1), 359 | A, D, F |
| 33 | 3 | 1 | CH | NMe$_2$ | 4-Me | CH | 5.1 | 337 (M + 1) | A, D, F |
| 34 | 3 | 1 | CH | NMe$_2$ | H | CH | 10.3 | 323 (M + 1) | A, D, F |
| 35 | 2 | 1 | CH | —N(piperazine)NMe | H | CH | 12.1 | 378 (M + 1) | A, D, G |
| 36 | 2 | 1 | CH | —N(piperazine)NMe | 4-Cl | CH | 5.6 | 412 (M + 1), 414 | A, D, G |
| 37 | 2 | 1 | CH | NEt$_2$ | H | CH | 6.5 | 351 (M + 1) | A, D, H |
| 38 | 2 | 1 | CH | NMe$_2$ | 4-Cl | CH | 4.4 | 357 (M + 1) | A, C, G |
| 39 | 4 | 2 | CH | —N(piperazine)NMe | 4-Cl | CH | 8.9 | 426 (M + 1), 428 | A, C, F |
| 40 | 4 | 2 | CH | NMe$_2$ | 4-Cl | CH | 3.9 | 371 (M + 1) | A, C, F |
| 41 | 2 | 2 | CH | —N(piperazine)NMe | 4-Cl | CH | 11 | 426 (M + 1), 428 | A, C, G |
| 42 | 4 | 1 | CH | —N(piperazine)NMe | H | N | 11.5 | 379 (M + 1) | A, D, G |

TABLE 3

Biological activity and mass spectra data of compound No. 43, 44

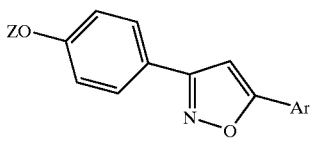

| No. | Z | Ar | IC$_{50}$ ($\mu$M) | MS | Methods |
|---|---|---|---|---|---|
| 43 |  | Ph | 5.3 | 349 (M + 1) | A, D, F |
| 44 | 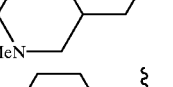 | Ph | 7.6 | 335 (M + 1) | Scheme 4 |

TABLE 4

Biological activity and mass spectra data of compound No. 45–48

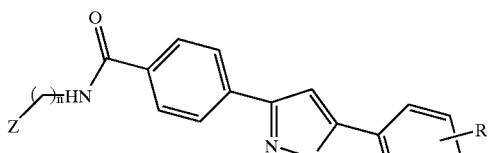

| No. | (CH$_2$)$_n$—Z | R | IC$_{50}$ | MS | Methods |
|---|---|---|---|---|---|
| 45 | (CH$_2$)$_3$NMe$_2$ | 4-Cl | 5.8 | 384 (M + 1) | Scheme 5 |
| 46 | 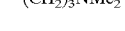 (CH$_2$)$_3$N⟨ ⟩NMe | 4-Cl | 6.1 | 439 (M + 1), 441 | Scheme 5 |
| 47 | (CH$_2$)$_3$N⟨ ⟩NMe | 4-OMe | 25 | 435 (M + 1) | Scheme 5 |
| 48 | (CH$_2$)$_3$NMe$_2$ | 4-OMe | 18.1 | 380 (M + 1) | Scheme 5 |

TABLE 5

Biological activity and mass spectra data of compound No. 49–53

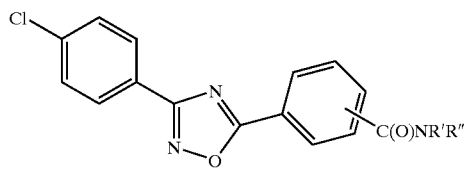

| No. | R' | R" | IC$_{50}$ | MS | Methods |
|---|---|---|---|---|---|
| 49 | H | (CH$_2$)$_3$NMe$_2$ | 4.7 | 385 (M + 1), 387 | Scheme 7 |
| 50 | H | (CH$_2$)$_3$N⟨ ⟩NMe | 6.7 | 440 (M + 1), 442 | Scheme 7 |

TABLE 5-continued

Biological activity and mass spectra data of compound No. 49–53

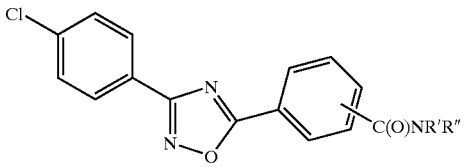

| No. | R' | R" | IC$_{50}$ | MS | Methods |
|---|---|---|---|---|---|
| 51 | Me | (CH$_2$)$_3$NMe$_2$ | 4.4 | 399 (M + 1), 401 | Scheme 7 |
| 52 | H | (CH$_2$)$_2$NMe$_2$ | 5.4 | 371 (M + 1), 373 | Scheme 7 |
| 53 | NR' R":  —N⟨ ⟩NMe | | 15.7 | 383 (M + 1), 385 | Scheme 7 |

TABLE 6

Biological activity and mass spectra data of compound No. 54, 55

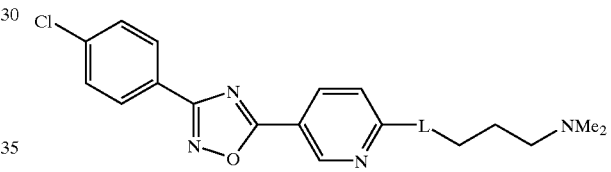

| No. | L | IC$_{50}$ | MS | Methods |
|---|---|---|---|---|
| 54 | NH | 5.35 | 358 (M + 1), 360 | K |
| 55 | O | 4.78 | 359 (M + 1), 361 | L |

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacological acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The following examples describe in detail the representative steps of the chemical synthesis of some compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

EXAMPLE 1

Preparation of 1-Chloro-3-[4-Methylpiperazin-1yl]Propane

N-Methyl piperazine (0.2 mol) and 1-bromo-3-chloropropane (0.1 mol) in toluene (100 mL) were heated at 80° C. for 3 hr. The precipitate was collected and the remaining filtrate extracted with HCl (1N, 2×50 mL). The aqueous layer was made basic with NaOH (1N) and extracted with ether (3×100 mL). The combined ether layers were washed with water, dried ($MgSO_4$), filtered and evaporated to afford product as a pale yellow oil.

EXAMPLE 2

Preparation of Oximes

4-Methoxybenzaldehyde (184 mmol), pyridine (400 mmol) and hydroxylamine hydrochloride (202 mmol) in methylene chloride (200 mL) were stirred at room temperature overnight. The reaction was washed with HCl (1N, 2×100 mL) and water (100 mL). The organic layer was dried ($MgSO_4$), filtered and evaporated to give crude oxime, which was utilized without purification.

EXAMPLE 3

Preparation of Chloro Oximes

Method A (K. Liu; B. Shelton; R. K. Howe *J. Org. Chem.,* 1980, 45, 3916)

To the oxime of Example 2 (42 mmol) in anh DMF (100 mL) at 0° C. under nitrogen, was added N-chlorosuccinimide (NCS, 45 mmol) in five portions over 30 min. The reaction was warmed to room temperature and stirred overnight. The reaction was poured into water (500 mL) and extracted with ether (3×150 mL). The combined organic layers were washed with water (2×150 mL) and brine (150 mL), dried ($MgSO_4$), filtered and evaporated to afford chloro oxime.

Method B (Gazz. Chim. Ital., 1984, 114, 131)

To 4-fluorobenzaldehyde oxime (7.2 mmol) in dioxane (20 mL) and conc HCl (10 mL) at 10° C., was added bleach (10.4 mL) dropwise over 5 minutes. After stirring at 10° C. for 5 min, the reaction was diluted with water (15 mL) and extracted with ether (50 mL). The ether layer was washed with water (25 mL) and brine (25 mL), dried ($MgSO_4$), and evaporated give pure chloro oxime.

Method C (S. Afr. J. Chem., 1986, 39, 54)

3-Chlorobenzaldehyde oxime (6.0 mmol, prepared from 3-chlorobenzaldehyde by a procedure analogous to that of Example 2) was dissolved in 1,2-dichloroethane (1,2-DCE) (30 mL) and 2-propanol (IPA)(7.5 mL), and was cooled to −12° C. t-Butylhypochlorite (7.4 mmol) was added in one portion. The solution initially turned dark orange but became colorless within a minute or so. After stirring for 15 minutes, the solvents were evaporated to afford chloro oxime.

EXAMPLE 4

Preparation of Substituted Phenoxyacetylenes

Step 1

TMS-acetylene (22.64 mmol) was added to a mixture of 4-iodophenoxyacetate (22.32 mmol), $(Ph_3P)_2PdCl_2$(0.078 mmol), CuI (0.16 mmol) in triethylamine (40 mL). The reaction was heated to 35° C. for 22 h, cooled and filtered. The solids were washed with ether (150 mL). The filtrate was washed with water (100 mL), brine (100 mL), dried ($Na_2SO_4$), filtered and evaporated to give the acetylene derivative as an off-white solid (5.10 g).

Step 2

NaOH (35.0 mmol) was added to a solution of the above acetylene derivative (17.22 mmol) in methanol (40 mL) and THF (8 mL). The reaction was stirred at room temperature for 16 h. Sat'd. ammonium chloride (40 mL) was added and the mixture extracted with ether (3×50 mL). The combined organic layers were washed with water (50 mL), brine (50 mL), dried (MgSO$_4$), filtered and evaporated. The crude material was immediately chromatographed on silica gel with 10% EtOAc/hexanes. BHT was added and the appropriate fractions were evaporated. Purified 4-hydroxyphenylacetylene was utilized immediately in the next reaction.

Step 3

A mixture of 4-hydroxyphenylacetylene (17.22 mmol), powdered potassium carbonate (68.88 mmol) and the title compound of Example 1 (17.23 mmol) in DMF (60 mL) were heated in an oil bath at 90° C. for 16 h. After cooling, water (300 mL) was added and the reaction extracted with ether (4×150 mL). The combined organic layers were washed with water, 1N NaOH, water and brine. Sodium carbonate and activated charcoal was added and then filtered through a pad of Celite. The filtrate was evaporated to afforded alkylated phenol.

Step 4

A solution of the chloro oxime of Example 3, Method B (1.5 mmol) in methylene chloride (3 mL) was added to a mixture of amine from Step 3 (0.5 mmol) and powdered 4A molecular sieves (1 g) in methylene chloride (2 mL). The reaction was stirred overnight at room temperature, and then filtered through a pad of Celite. The pad of Celite was washed with methanol (25 mL). This collected filtrate was passed through a column of Bio-Rad AG 50W-X2 (5 g). The column was washed with methanol (30 mL) and the product eluated from the column with 2M NH$_3$/MeOH (30 mL). The ammonical fractions were evaporated to afford cycloadduct.

EXAMPLE 5
Preparation of Isoxazoles

To the chloro oxime of Example 3, Method A (4.3 mmol) and phenylacetylene (4.3 mmol) in ethyl acetate (10 mL), was added dropwise over several minutes triethylamine (4.5 mmol) in ethyl acetate (10 mL). The reaction was stirred at room temperature overnight and then poured into water (15 mL) and ether (15 mL). The organic layer was dried (MgSO$_4$), filtered and evaporated to afford crude cycloadduct. This was purified by recrystallization from hexane.

Example 6
Preparation of Phenol

Method D

To methyl ether from Example 5 (3.1 mmol) in methylene chloride (15 mL) at 0° C. under a nitrogen atmosphere, was added boron tribromide (1 M in methylene chloride, 6.2 mmol) over several minutes. The reaction was warmed to room temperature, stirred overnight, and carefully poured into ice-water (50 mL). The precipitated product was isolated by filtration.

EXAMPLE 7
Preparation of Amines

Method F

To the phenol of Example 6 (1.2 mmol) in anh DMF (5 mL), was added freshly crushed potassium carbonate (2.5 mmol). The reaction was stirred at room temperature for 30 min. N-(3-chloropropyl)-piperidine hydrochloride (1.5 mmol) was added and the reaction heated to 90–100° C. overnight. The reaction was then added to water (25 mL) and extracted with ethyl acetate (3×15 mL). The combined organic layers were washed with water (3×15 mL), 1 N NaOH (15 mL) and brine (15 mL), dried (MgSO$_4$), filtered and evaporated to provide the amine.

Method G

To 5-phenyl-3-(2-hydroxyphenyl)isoxazole (0.8 mmol, prepared by a procedure analogous to that of Example 6) in anh DMF (5 mL), was added sodium hydride (1.0 mmol). The reaction was stirred at room temperature for 15 min. The compound of Example 1 (1.2 mmol) was added and the reaction heated to 90–100° C. overnight. The reaction was then added to water (50 mL) with stirring. The aqueous layer was extracted with ethyl acetate (3×100 mL). The combined organic layers were washed with water (3×100 mL), dried (MgSO$_4$), filtered and evaporated. The crude amine was purified by conversion into the hydrochloride salt.

Method H

To 5-phenyl-3-(2-hydroxyphenyl)isoxazole (1.3 mmol, prepared by a procedure analogous to that of Example 6) in anh DMF (5 mL) at room temperature under nitrogen, was added sodium hydride (1.5 mmol). After stirring for 20 min, 1-bromo-3-chloropropane (1.5 mmol) was added. The reaction was heated at 90–100° C. overnight. The reaction was poured into water (50 mL) and extracted with ether (2×75 mL). The combined organic layers were washed with water, dried (MgSO$_4$), filtered and evaporated. This alkyl halide (0.9 mmol) and diethylamine (7 mmol) in anh DMF (5 mL) were heated at 80° C. overnight. The reaction was poured into water (100 mL) and extracted with ethyl acetate. The organic layer was washed with water, dried (MgSO$_4$), filtered and evaporated to an oil. This was converted into the hydrochloride salt and recrystallized from a mixture of methylene chloride and ether.

EXAMPLE 8
Preparation of Amide Oximes

A mixture of 4-chlorobenzonitrile (0.1 mol) and hydroxylamine (50% aqueous; 0.163 mol) in ethanol (100 mL) was heated to reflux for 16 h. After cooling to room temperature, cold water (500 mL) was added. The solids were filtered, washed with water and dried to give the amide oxime.

EXAMPLE 9
Preparation of Oxadiazoles

Method I

A solution of 4-methoxy benzoic acid chloride (30.0 mmol) in pyridine (10 mL) was added to a solution of the amide oxime of Example 8 (30.0 mmol) in pyridine (10 mL). The resulting solution became hot. The reaction was heated at reflux for 30 minutes. Upon cooling, water (100 mL) was added and the solid collected by filtration, washed with water and dried. The compound was recrystallized from ethanol. The methyl ester was deprotected with boron tribromide by a procedure analogous to that of Example 6, Method D.

Method J

A mixture of the amide oxime of Example 8 (2.00 mmol), 4-hydroxy-3-methoxybenzoic acid (2.00 mmol), and EDCl (2.00 mmol) in diglyme (6 mL) was heated to 50° C. overnight and then to 110° C. for 4 hours. Water (30 mL) was added to the cooled reaction mixture and the aqueous was extracted with ethyl acetate (3×15 mL). The combined organic layers were washed with several portions of water, brine, dried (MgSO$_4$), filtered and evaporated. The phenol can be purified by silica gel chromatography.

EXAMPLE 10
Preparation of Isoxazole Amides 5-(4-Chlorophenyl)-3-(4-carbomethoxyphenyl)isoxazole (1.2 mmol, prepared from the appropriate starting materials by a procedure analogous to that of Example 5) and sodium hydroxide (5 mL; 1 N) in methanol (50 mL) were heated in an oil bath at 60° C for 4.5 h. After cooling, the methanol was evaporated and the aqueous residue acidified to pH=1 with conc hydrochloric acid. The solid was collected, washed with water and dried. To this acid (1.0 mmol) and 2 drops of DMF in methylene chloride (50 mL), was added oxalyl chloride (2 M in CH$_2$Cl$_2$; 0.6 mL). The reaction was stirred at room temperature for 2 hours. N,N-Dimethyl-1,3-propanediamine (2.4 mmol) was added. After stirring overnight, the reaction was poured into sodium hydroxide (1 N; 50 mL) and extracted. The basic aqueous layer was extracted with an additional portion of methylene chloride. The combined organic layers were washed with water, dried (MgSO$_4$), filtered and evaporated. Pure amide was obtained upon recrystallization from a mixture of methylene chloride and hexanes.

EXAMPLE 11
Preparation of Oxadiazole Amides

Methyl 4-chlorocarbonyl benzoate (5.99 mmol) was added to a solution of the amide oxime of Example 8 (5.98 mmol) in pyridine (4 mL). The reaction was heated to reflux for 30 minutes. After cooling, water (20 mL) was added to the reaction. The resulting solid was filtered, washed with water and dried to give ester. To this ester in dioxane/water (25 mL/10 mL), was added lithium hydroxide (6.01 mmol). The reaction was stirred at room temperature overnight. The reaction was cooled to 0° C., acidified to pH=1 with HCl (10 N). Additional water (20 mL) was added and the resulting solid filtered, washed with water and dried to afford acid. Oxalyl chloride (0.65 mL; 2.0 M in CH$_2$Cl$_2$; 1.30 mmol) was added to a suspension of acid (0.67 mmol) in methylene chloride (5 mL). DMF (1 drop) was added resulting in immediate gas evolution. After 2 h, the suspension became a solution. The volatiles were evaporated to give the acid chloride. This was redissolved in methylene chloride (5 mL) and then N,N-dimethylethylenediamine was added (2.00 mmol). After stirring at room temperature overnight, the reaction mixture was diluted with ethyl acetate, washed with satd sodium bicarbonate (aq), water and brine. The organic layer was dried, filtered and evaporated to afford the oxadiazole amide.

EXAMPLE 12
Preparation of 5-Pyridyloxadiazoles

Step 1

6-Chloronicotinoyl chloride (3.00 mmol) was added to a solution of the amide oxime of Example 8 (3.00 mmol) in pyridine (2 mL) to give a thick slurry. This was heated to reflux for 30 minutes. The reaction was cooled and cold water was added (10 mL). The solid was filtered, washed with water and dried to afford the oxadiazole (a compound of Formula 29 in Scheme 8).

Step 2

Method K

The oxadiazole from Step 1 (0.51 mmol) in 3-dimethylaminopropylamine (2 mL) was heated to 120° C. for 14 hours. After cooling, the reaction was added to cold water (15 mL), and the resulting solid was filtered, washed with water and dried to afford amine.

Method L

A mixture of NaH (60% in oil, 1.38 mmol) and 3-dimethylamino-1-propanol (1.35 mmol) in DMF (3 mL) was heated to 50° C. for 15 minutes. After cooling to room temperature, the oxadiazole from Step 1 (0.68 mmol) was added. After 2 hours, the reaction was added to cold water (15 mL), the solid filtered, washed with water and dried. This was chromatographed to give pure amine.

The invention has been described in detail with particular reference to the above embodiments thereof. The above embodiments and examples are given to illustrate the scope and spirit of the present invention. These embodiments and examples will make apparent, to those skilled in the art, other embodiments and examples. These other embodiments and examples are within the contemplation of the present invention. It will be understood that variations and modifications can be effected within the spirit and scope of the invention; therefore, the instant invention should be limited only by the appended claims.

We claim:

1. A compound of Formula (I) or (II),

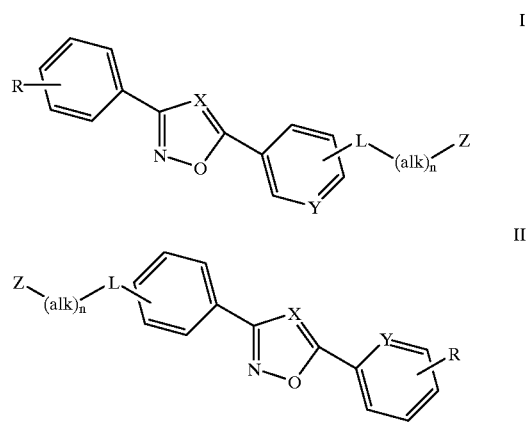

wherein

R is one or two independent members selected from hydrogen, halogen, C$_{1-6}$ alkyl, C$_{1-6}$ alkoxy, alkoxycarbonyl, aryl, aryloxy, hydroxy, nitro, sulfonylamino, trifluoromethyl, and cyano, and methylenedioxy and ethylenedioxy where two adjacent R members form these dioxy rings;

X is nitrogen or CR$_1$ wherein R$_1$ is selected from hydrogen, alkyl, aryl, halogen, CH$_2$OH, carbomethoxy, and carboethoxy;

Y is CR or nitrogen, provided that when X is nitrogen then Y is nitrogen;

L is selected from oxygen, sulfur, —N(R$_2$)—, —C(O) NR$_2$—, —R$_2$NC(O)—, —C(O)O—, and —OC(O)—, wherein R$_2$ is hydrogen or C$_{1-6}$ alkyl; and Z is a piperazino ring;

Alk is a branched or unbranched alkyl group;

n is an integer from 0–6 representing the number of carbons in the alkylene group, with the proviso that when L is oxygen, sulfur, or nitrogen, n is an integer from 2–6;

or an optical isomer, enantiomer, diastereomer, racemate or racemic mixture thereof, or a pharmaceutically acceptable salt thereof.

2. The compound of claim 1 wherein R is one or two independent members selected from hydrogen, halogen, C$_{1-6}$alkyl, C$_{1-6}$alkoxy, alkoxycarbonyl, phenyl, phenyloxy, hydroxy, nitro, sulfonylamino, trifluoromethyl, cyano, methylenedioxy, and ethylenedioxy.

3. The compound of claim 1 wherein X is CH.

4. The compound of claim 3 wherein Z is

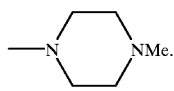

5. The compound of claim 1 which is represented by Formula (II),

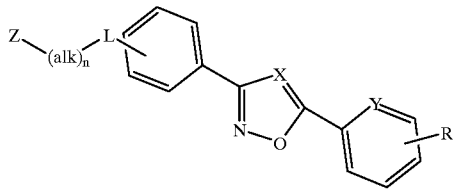

wherein Z, L, X, Y, R, and n are as claimed in claim 1.

6. The compound of claim 5 wherein X is CH and Z is

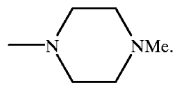

7. The compound of claim 6 wherein R is halogen.

8. The compound of claim 7 wherein R is 4-Cl.

9. A compound of claim 1 or a pharmaceutically acceptable salt thereof, which is piperazine, 1-[3-[4-[5-(4-chlorophenyl)-3-isoxazolyl]phenoxy]propyl]-4-methyl-.

10. A compound of claim 1 or a pharmaceutically acceptable salt thereof, which is piperazine, 1-[3-[4-[3-(4-chlorophenyl)-5-isoxazolyl]phenoxy]propyl]-4-methyl-.

11. A compound of claim 1 or a pharmaceutically acceptable salt thereof, which is piperazine, 1-[3-[4-[3-[4-(1,1-dimethylethyl)phenyl]-5 -isoxazolyl]phenoxy]propyl]-4-methyl-.

12. A compound of claim 1 or a pharmaceutically acceptable salt thereof, which is piperazine, 1-[3-[4-[3-[4-chloro-3-(trifluoromethyl)phenyl]-5 -isoxazolyl]phenoxy]propyl]-4-methyl-.

13. A compound of claim I or a pharmaceutically acceptable salt thereof, which is piperazine, 1 -[3-[4-[3-(4-fluorophenyl)-5-isoxazolyl]phenoxy]propyl]-4-methyl-.

14. A pharmaceutical composition comprising a compound of claim 1 and a pharmaceutically acceptable carrier.

15. A method of treating a subject having inflammation caused by or contributed to by action of IL-8, which comprises administering to said subject a therapeutically effective amount of the compound of Formula (I) or (II) as defined in claim 1.

* * * * *